(12) United States Patent
Carman et al.

(10) Patent No.: US 9,138,336 B2
(45) Date of Patent: Sep. 22, 2015

(54) EXPANDABLE DISTENSION DEVICE FOR HOLLOW ORGAN GROWTH

(75) Inventors: Gregory Paul Carman, Los Angeles, CA (US); James C. Y. Dunn, Santa Monica, CA (US); Mohanchandra Kotekar Panduranga, North Hills, CA (US); Shant Shekherdimian, Tujunga, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 824 days.

(21) Appl. No.: 13/252,790

(22) Filed: Oct. 4, 2011

(65) Prior Publication Data
US 2012/0083820 A1      Apr. 5, 2012

Related U.S. Application Data

(63) Continuation of application No. PCT/US2010/032106, filed on Apr. 22, 2010.

(60) Provisional application No. 61/171,799, filed on Apr. 22, 2009.

(51) Int. Cl.
| | |
|---|---|
| A61F 2/86 | (2013.01) |
| A61F 2/88 | (2006.01) |
| A61B 17/11 | (2006.01) |
| A61B 17/00 | (2006.01) |
| A61F 2/848 | (2013.01) |
| A61M 25/01 | (2006.01) |

(52) U.S. Cl.
CPC . *A61F 2/88* (2013.01); *A61B 17/11* (2013.01); *A61B 2017/00004* (2013.01); *A61B 2017/00818* (2013.01); *A61B 2017/1132* (2013.01); *A61F 2/848* (2013.01); *A61F 2250/0039* (2013.01); *A61M 25/0102* (2013.01)

(58) Field of Classification Search
CPC ............... A61B 17/11; A61B 2017/00818; A61B 2017/1132; A61F 2/04; A61F 2/82; A61F 2/848; A61F 2/88; A61F 2002/044; A61F 2/045
USPC ............ 606/191; 623/1.13, 1.15, 1.16, 1.18, 623/1.19, 1.2, 1.22
See application file for complete search history.

(56) References Cited

U.S. PATENT DOCUMENTS

| | | | | |
|---|---|---|---|---|
| 5,415,660 | A * | 5/1995 | Campbell et al. | 606/62 |
| 5,769,893 | A * | 6/1998 | Shah | 424/423 |

(Continued)

OTHER PUBLICATIONS

Korean Intellectual Property Office, international search report and written opinion issued on Jan. 21, 2011, including claims searched, for counterpart PCT Application No. PCT/US10/032106, pp. 1-15.

(Continued)

*Primary Examiner* — Ryan Severson
(74) *Attorney, Agent, or Firm* — John P. O'Banion

(57) ABSTRACT

An expandable mechanical distension device for hollow organ growth comprising a spring stent structure to elongate hollow organs by mechanical expansion. The device preferably expands radially to engage the internal walls of the hollow organ segment at a desired treatment location and expands axially to enlarge the hollow organ segment. The distension device may be configured for the treatment of patients with insufficient hollow viscus, e.g. hollow organ deficiency such as short gut syndrome, to enhance their gut length by mechanical force.

24 Claims, 9 Drawing Sheets

(56) References Cited

U.S. PATENT DOCUMENTS

| | | | | |
|---|---|---|---|---|
| 6,033,436 | A * | 3/2000 | Steinke et al. | 623/1.15 |
| 6,210,432 | B1 * | 4/2001 | Solem et al. | 623/1.15 |
| 6,641,576 | B1 * | 11/2003 | Vito et al. | 606/1 |
| 6,699,176 | B1 * | 3/2004 | Khouri | 600/38 |
| 7,018,402 | B2 * | 3/2006 | Vito et al. | 623/1.15 |
| 7,192,443 | B2 * | 3/2007 | Solem et al. | 623/2.37 |
| 7,300,455 | B2 | 11/2007 | Vito et al. | |
| 7,458,986 | B2 | 12/2008 | Schmitt | |
| 8,268,009 | B2 * | 9/2012 | Teitelbaum et al. | 623/23.64 |
| 2002/0133223 | A1 * | 9/2002 | Vito et al. | 623/1.18 |
| 2003/0040803 | A1 * | 2/2003 | Rioux et al. | 623/23.7 |
| 2003/0083736 | A1 * | 5/2003 | Brown et al. | 623/1.16 |
| 2003/0135267 | A1 * | 7/2003 | Solem et al. | 623/1.18 |
| 2003/0144730 | A1 * | 7/2003 | Datta et al. | 623/1.16 |
| 2005/0010191 | A1 | 1/2005 | Skinner et al. | |
| 2005/0182481 | A1 | 8/2005 | Schlick et al. | |
| 2007/0173926 | A1 * | 7/2007 | Bobo et al. | 623/1.16 |
| 2007/0185572 | A1 * | 8/2007 | Solem et al. | 623/2.37 |
| 2008/0195224 | A1 | 8/2008 | Teitelbaum et al. | |
| 2009/0240339 | A1 * | 9/2009 | Teitelbaum et al. | 623/23.64 |
| 2012/0083820 | A1 * | 4/2012 | Carman et al. | 606/191 |

OTHER PUBLICATIONS

Saday et al.—"A Surgical Model to Increase the Intestinal Absorptive Surface: Intestinal Lengthening and Growing Neomucosa in the Same Approach"—Jour. of Surgical Research, vol. 62, article 0193, 1996, pp. 184-191.

Sudan et al.—"Comparison of Intestinal Lengthening Procedures for Patients with Short Bowel Syndrome"—Annals of Surgery, vol. 246, No. 4, Oct. 2007, pp. 593-604.

Chen et al.—"An animal experiment on short gut lengthening"—Chinese Medical Journal, vol. 110, No. 5, 1997, pp. 354-357.

Park, J. et al.—"Enterogenesis by Mechanical Lengthening: Morphology and Function of the Lengthened Small Intestine"—Jour. of Pediatric Surgery, vol. 39, No. 12, Dec. 2004, pp. 1823-1827.

Safford, S.D. et al.—"Longitudinal mechanical tension induces growth in the small bowel of juvenile rats"—Gut, vol. 54, pp. 1085-1090, 2005.

Printz, H. et al.—"Small Bowel Lengthening by Mechanical Distraction"—Digestion, vol. 58, 1997, pp. 240-248.

Shekherdimian, S. et al.—"Intestinal lengthening in rats after massive small intestinal resection"—Surgery, vol. 146, No. 2, Aug. 2009, pp. 291-295.

Shekherdimian, S. et al.—"The feasibility of using an endoluminal device for intestinal lengthening"—Jour. of Pediatric Surgery, vol. 45, 2010, pp. 1575-1580.

Mendoza, J. et al.—"Contractile Function of the Mechanically Lengthened Intestine"—Jour. of Surgical Research, vol. 136, 2006, pp. 8-12.

Chang, P. et al.—"Sustainability of mechanically lengthened bowel in rats"—Jour. of Pediatric Surgery, col. 41, 2006, pp. 2019-2022.

* cited by examiner

EXPANDABLE DISTENSION DEVICE FOR HOLLOW ORGAN GROWTH

CROSS-REFERENCE TO RELATED APPLICATIONS

This application a 35 U.S.C. §111(a) continuation of PCT international application number PCT/US2010/032106 filed on Apr. 22, 2010, incorporated herein by reference in its entirety, which is a nonprovisional of U.S. provisional patent application Ser. No. 61/171,799 filed on Apr. 22, 2009, incorporated by reference herein in its entirety. Priority is claimed to each of the foregoing applications.

The above-referenced PCT international application was published as PCT International Publication No. WO 2010/124126 published on Oct. 28, 2010 and republished on Mar. 31, 2011, and is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to a mechanical distention device and methods, and more particularly to a mechanical distension device for manipulating hollow organ growth.

2. Description of Related Art

Short bowel syndrome (SBS), also known as short gut syndrome, occurs in patients with insufficient length of intestine to maintain normal digestion and absorption. In the US alone more than 100,000 patients suffer from this life threatening disease every year. SBS is a condition that results in malnutrition, malabsorption and dehydration due to loss of large amounts of intestinal tissue. Typically, symptoms appear with greater than 70% of small bowel loss, although this varies and often depends on the presence of an ileocecal valve. The most common causes of SBS in the pediatric population are necrotizing enterocolitis, intestinal atresias, volvulus and abdominal wall defects.

Currently, the treatment for SBS includes medical therapy with total parenteral nutrition to provide necessary nutrients and hydration, and surgical therapy to increase absorption capacity and decrease transit time.

Surgical treatment options for SBS include procedures that increase length, slow down transit time and intestinal transplantation. These procedures have thus far been met with limited success and are associated with significant complications. Hyperalimentation via the parenteral route remains the mainstay of treatment, but is associated with significant complications which include catheter related infections, liver failure and osteoporosis. In addition, the management of patients with SBS is associated with a significant financial burden, with the average cost of care for the first year of management averaging over $500,000 per patient and subsequently home care alone surpassing $100,000 dollars per patient annually.

Recently however, the concept of using mechanical force to lengthen intestinal tissue has been studied using a variety of tissue expander devices. Several methods of applying mechanical force to an intestinal segment have been developed, including repeated injections of saline solution, gradual advancement of a screw, and use of a hydraulic piston. Many of these methods require repeated interventions such as serial screw advancements or saline injections. In addition, all of these techniques incorporate a device that is at least partly outside the abdominal cavity, introducing risks such as dislodgement, damage to the exterior component, infection, fistula formation and increased inflammation and adhesions making potential re-implantation of isolated segments very difficult. Furthermore, because these devices deliver force in only one direction, the ability to lengthen intestinal segments is limited by the confines of the abdominal cavity.

Accordingly, an object of the present invention is a method to achieve intestinal lengthening using a completely internal device that does not require repeated interventions during the lengthening procedure. At least some of these objectives will be met in the description described herein.

BRIEF SUMMARY OF THE INVENTION

The present invention generally comprises an expandable mechanical distension device for hollow organ growth. By way of example, and not of limitation, the invention includes a medical device using biomaterials including nickel titanium, stainless steel, or bio-degradable shape memory polymer, to elongate hollow organs by mechanical expansion. The device preferably expands radially to engage the internal walls of the hollow organ segment at the desired location and expands axially to enlarge the hollow organ segment. The distension device may be configured for the treatment of patients with insufficient hollow viscus, e.g. hollow organ deficiency such as short gut syndrome, to enhance their gut length by mechanical force.

The mechanical distension device of the present invention may be made of shape memory materials preferably nickel-titanium or biocompatible/biodegradable shape memory polymers is proposed. The device may employ spring like structures built using a wire or sheets to produce tensile stresses in the intestinal system. In one embodiment, various shapes for the structure may be used to aide in collapsing the device into a smaller diameter so that it can be deployed using an endoscope.

For example, the collapsed device/spring is compressed into its minimum size using degradable suture to hold it axially in place and subsequently placed in a special tube similar to a catheter with push rod. The device can be delivered into any portion of the body passage using endoscope and deployed by pushing the device with the push rod into the intestinal tract. Upon deployment of the device into the intestinal tract, the ends of the device engages the interior of the body passage holding it in a specific location and enabling it to transfer stresses to that particular location of the intestine while the suture prevents immediate elongation of the device. After a period of time, the degradable suture dissolves and the structure expands along the longitudinal direction thereby producing longitudinal forces in the growth direction of the intestine. The device is anchored at the end locations producing elongation forces on the intestine. The body passage is examined periodically to check the length extension of the portion of the intestines. After a sufficient period, the device can be retracted from the body passage using endoscope or as an option can be left in the body.

An aspect of the invention is a mechanical distension apparatus, comprising an elongate, tubular structure configured to be inserted into a body lumen at a at a treatment location within the lumen. The tubular structure has a central axial channel configured to allow normal operation of said lumen, and first and second ends and being compressible along a longitudinal axis between said ends to form an axially compressed configuration. The tubular structure further includes at least two spaced apart anchor portions configured to engage an internal wall of the lumen at said treatment location while in said axially compressed configuration, wherein the tubular structure is biased to elongate to an expanded configuration, the bias configured to impart a force on the lumen at said treatment location to lengthen the lumen at said location.

Another aspect is a distension system for lengthening a segment of a luminal hollow organ comprising the above described tubular structure and an absorbable retaining element configured to retain the tubular structure in its axially compressed configuration, wherein the retaining element is configured to dissolve after a period of time within the lumen to free the tubular structure to impart said force on said lumen.

Another aspect is a method for distending a hollow organ comprising the steps of providing the above-described tubular structure to at a treatment location within the organ, compressing said tubular structure along a longitudinal axis of the tubular structure, retaining the tubular structure in an axially compressed state with a dissolvable suture material, inserting the compressed tubular structure into the organ and positioning the tubular structure adjacent the location wherein the at least two anchor portions engage the organ and hold the tubular structure in position; and expanding the tubular structure to an expanded configuration to lengthen the organ at said treatment location.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

Figure 8B:
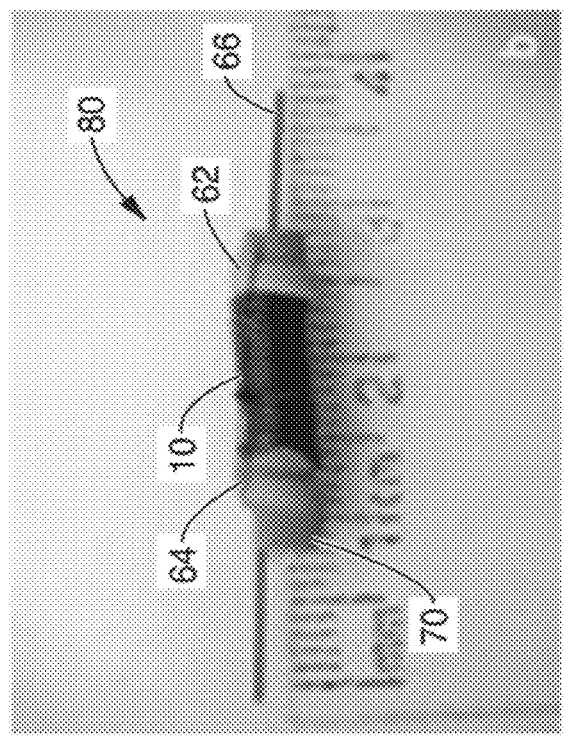
Figure 8A:
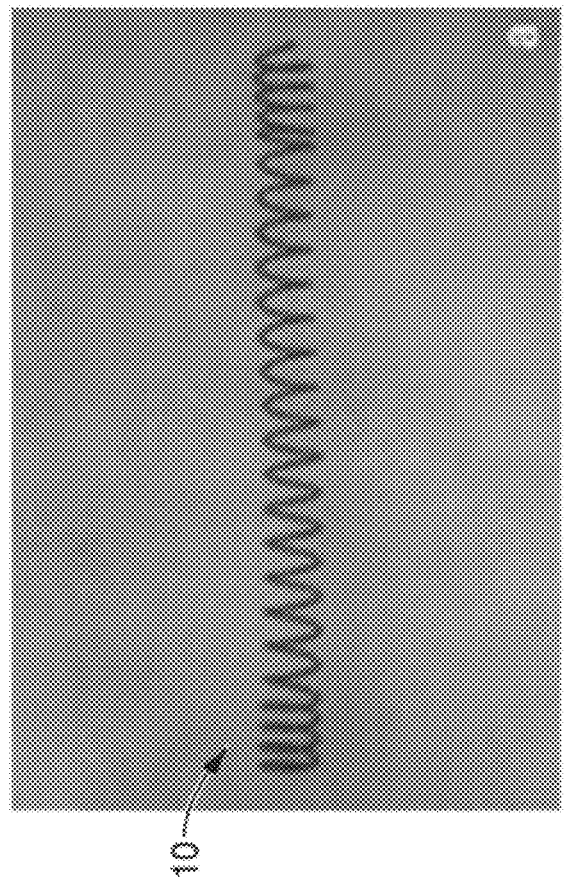

FIG. 8A-B show a test setup of the distension system of the present invention using a nickel titanium spring (FIG. 8A) and tissue expansion system in a deployable configuration (FIG. 8B).

Figure 9:
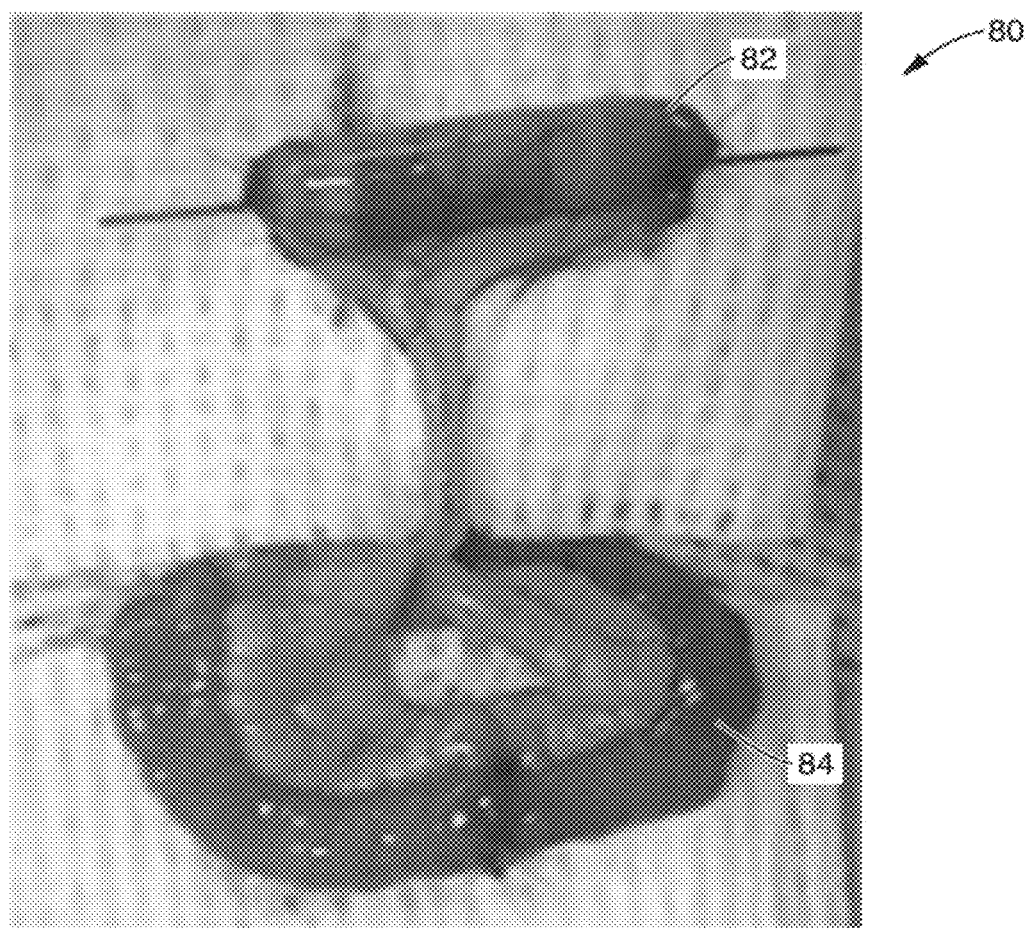

FIG. 9 is a photograph taken intra-operatively demonstrating the implanted tissue expansion device of the present invention in an isolated intestinal segment attached to native blood supply and restoration of bowel continuity.

Figure 10C:
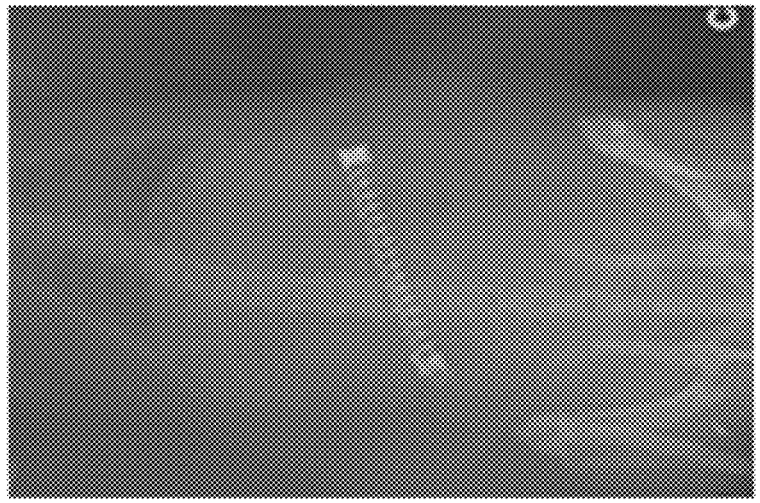
Figure 10B:
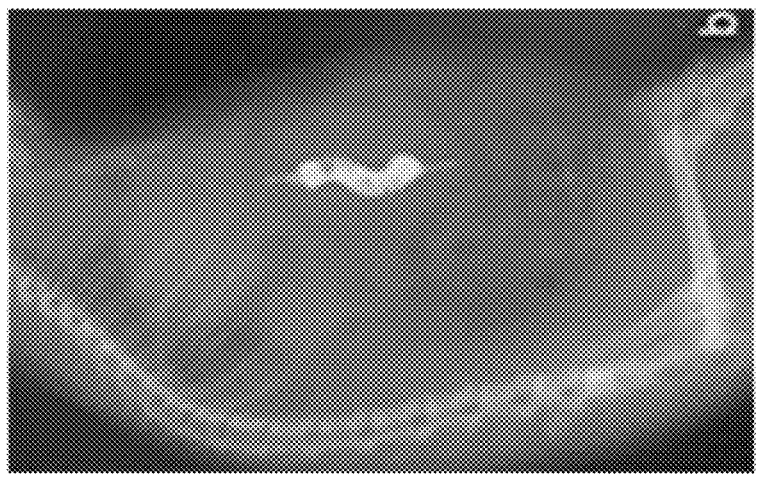
Figure 10A:
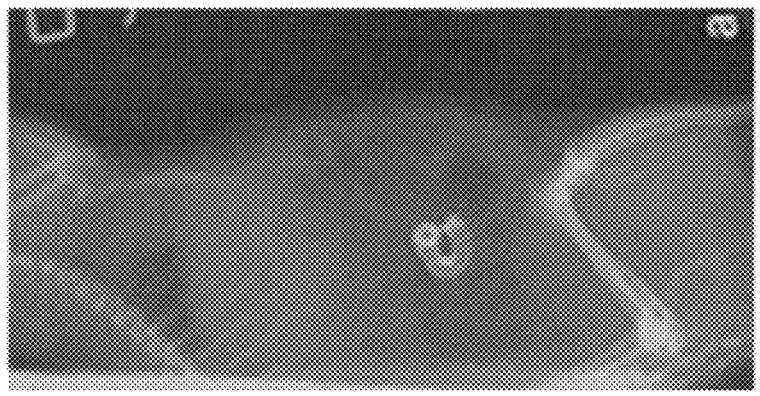

FIG. 10A-C are a series of x-rays demonstrating spring buckling in the absence of an axial support structure (FIG. 10A), in comparison to the distension system of the present invention with a straight wire stent in a compressed configuration (FIG. 10B) and fully extended configuration (FIG. 10C).

Figure 11A:
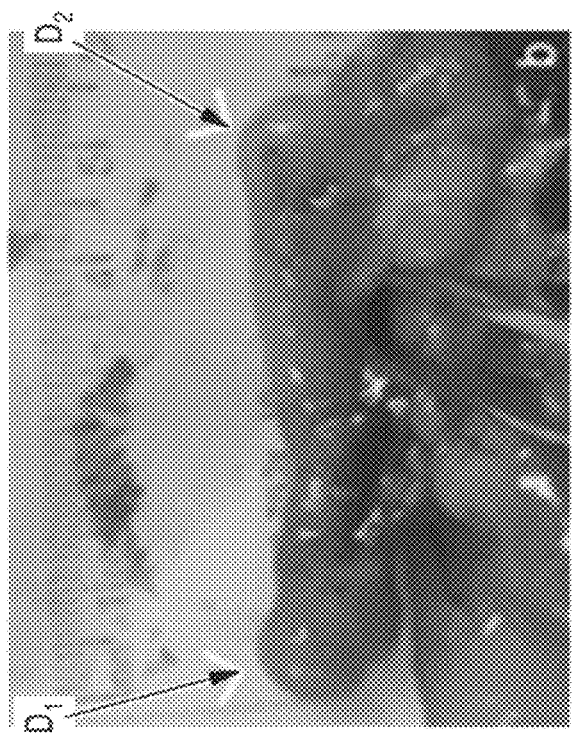
Figure 11B:
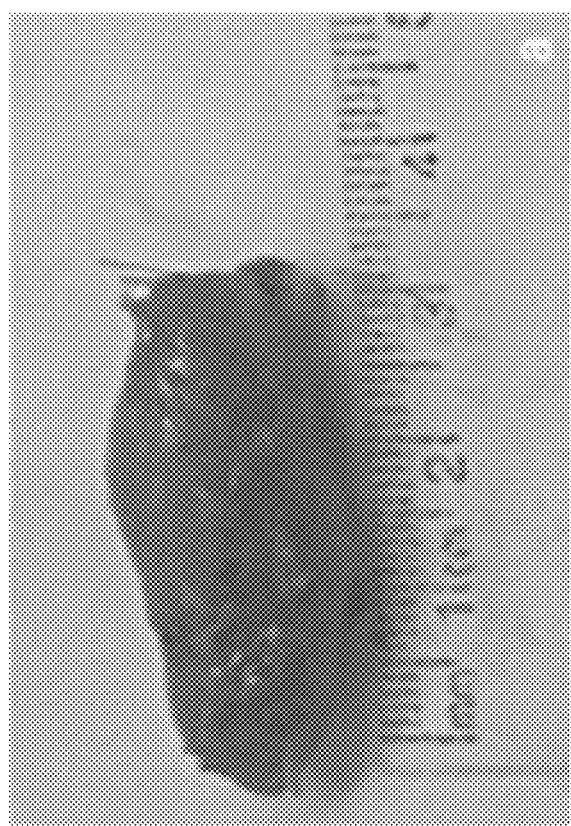

FIGS. 11A-B show photographs of final intestinal segments in control (FIG. 11A) and experimental (FIG. 11B) organ segments.

Figure 12A:
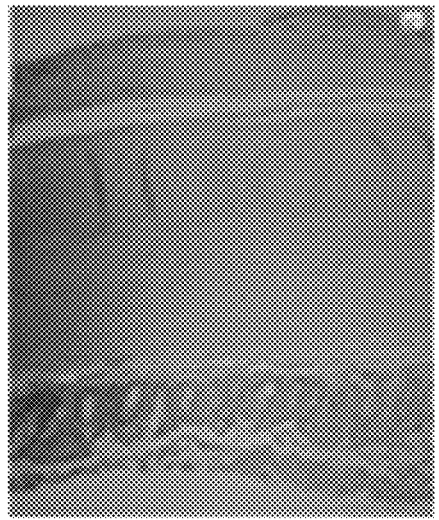
Figure 12B:
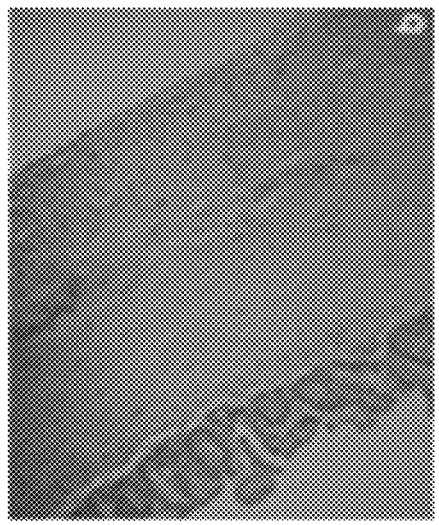
Figure 12C:
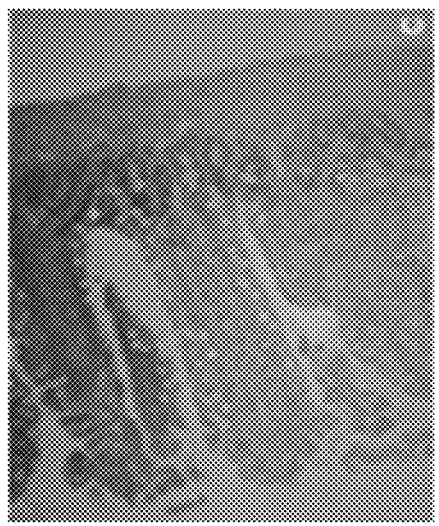

FIGS. 12 A-C are images of hematoxylin and eosin staining of intestinal segments depicting preserved intestinal architecture with muscular hypertrophy and villous atrophy in both control (FIG. 12A) and lengthened (FIG. 12B) segments in comparison to in-continuity (FIG. 12C) jejunum.

DETAILED DESCRIPTION OF THE INVENTION

Referring more specifically to the drawings, for illustrative purposes the present invention is embodied in the apparatus generally shown in FIG. 1 through FIG. 12C. It will be appreciated that the apparatus may vary as to configuration and as to details of the parts, and that the method may vary as to the specific steps and sequence, without departing from the basic concepts as disclosed herein.

Figure 1:
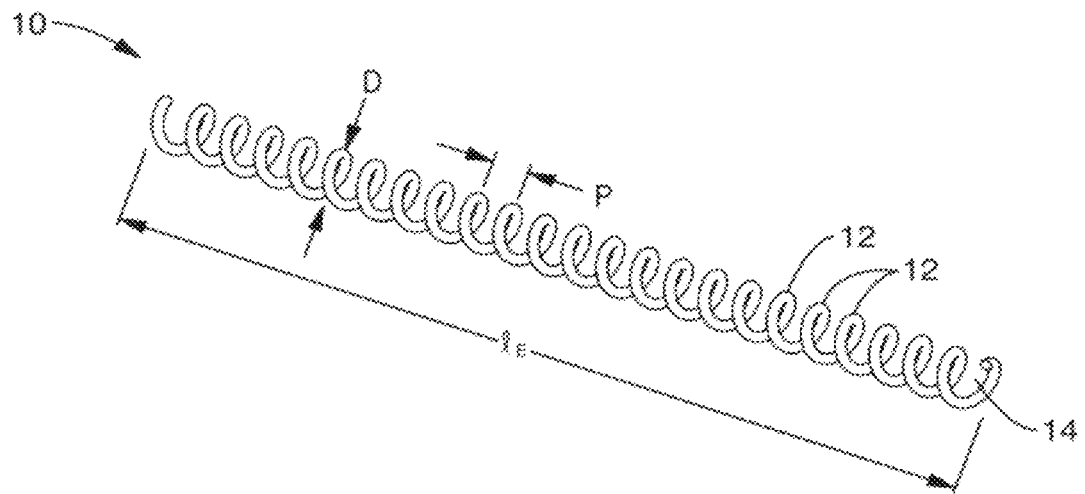
FIG. 1 illustrates a perspective view of the spring distension device in accordance with the present invention.

FIG. 1 illustrates a perspective view of the spring distension device 10 in accordance with the present invention. The extension device 10 is a spring stent structure capable of multi-fold (5-10 times) expansion from a compressed state. Distension spring 10 comprises a plurality of coils 12 wound to have a diameter D sized to substantially match the internal diameter of the lumen to be treated. The spring stent 10 is an open structure with a central channel 14 to allow for normal passage of solids/liquids (e.g. food through the colon) and normal operation of the lumen (e.g. digestion absorption through the intestinal walls).

The gauge and pitch P of the spring stent 10 may be sized to vary the force applied by the stent. For example, spring stent 10 may have a diameter sized D for optimal engagement with the internal walls of the lumen while in its radially expanded form. To achieve the appropriate distension force, the gauge of the wire 10 and/or pitch P may be increased to increase the force applied by a spring of the set diameter D. The fully expanded length $l_e$ of the spring stent 10 is configured to provide the desired level of distension of the organ upon expansion.

Figure 2:
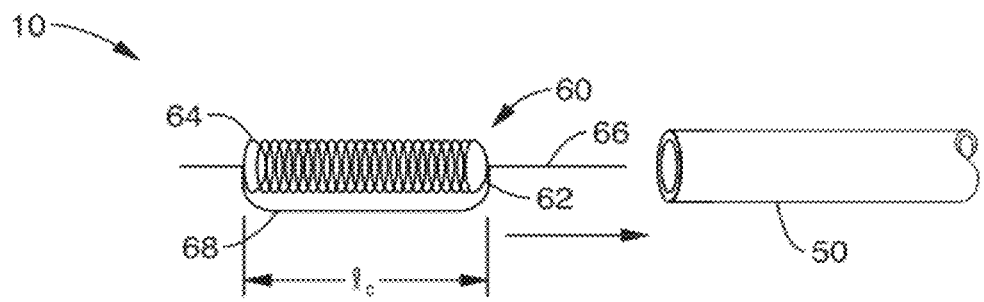
FIG. 2 is a schematic view of a system for mechanical distention of a hollow organ using the distension spring of FIG. 1.

FIG. 2 is a schematic view of a system 60 for mechanical distention of a hollow organ using the distension spring 10. Spring stent 10 is shown wound in a compressed state (length $l_c$) and held together with an absorbable suture 68. The spring 10 also comprises end caps 62 and 64, e.g. latex catheter tips, which facilitate delivery into the treatment location in the lumen. The end caps 62 and 64 may also be configured to engage the walls to anchor the ends of the spring at the desired locations within the lumen.

It is appreciated that other radial expansion means, e.g. a non-degradable inflatable ring bladder (not shown), or other retractable structure, may be used to affect anchoring of the ends of the spring stent 10 into the lumen walls.

The spring stent 10 may be disposed around an axial or longitudinal support 66 to avoid buckling of the spring. The longitudinal support 66 preferably comprises a flexible metal wire (or other non-absorbable biocompatible material) having sufficient rigidity to withstand lateral buckling forces imposed by the spring stent 10, and may have sufficient length to accommodate the expansion of the spring stent 10.

The system 60 may further include tube 50, which has an inner radius sized to house the spring stent 10 and deliver it to the appropriate location in the lumen. The inside radius of the tube 50 may be sized to house the spring stent 10 in a radially compressed configuration during delivery to the treatment location in the lumen.

Tube 50 may be a catheter or the like, wherein the stent 10 is pushed out of the distal end of tube 50 via a push rod (not shown) or the like. Tube 50 may also comprise a section of dissolvable or absorbable material that dissolves after a short period of time in the lumen, releasing the spring stent 10 in a radially expanded configuration such that the ends of the stent 10 engage the wall and begin to exert a tensile stress along the lumen axis.

In a preferred method for lengthening a bowel segment in accordance with the present invention, a collapsed spring stent 10 is compressed into its minimum size using degradable suture 68 to hold it axially in place and subsequently placed in a tube 50 (e.g. catheter) with push rod (not shown). The spring stent 10 can be delivered into any portion of the body passage using endoscope and deployed by pushing the device with the push rod into the intestinal tract. Upon deployment of the spring stent 10 into the intestinal tract, the spring stent 10 engages the interior of the body passage at its ends, holding it in a specific location and enabling it to transfer stresses to that particular location of the intestine. After a period of time, the degradable suture 68 dissolves and the spring stent 10 expands along the longitudinal direction. The spring stent 10 is anchored at specific locations producing elongation forces on the intestine. The body passage may be examined periodically to check the length extension of the portion of the intestines. After a sufficient period, the spring stent 10 may then be retracted from the body passage using endoscope, or as an option can be left in the body.

In an alternative embodiment, a section of the lumen (e.g. bowel) is transected, and the distension system 60 is installed in a compressed configuration (via an absorbable suture 68) into the de-functional limb. End to side anastomosis is then performed to encase the distension system in the lumen. When the suture 68 dissolves, the spring 20 exerts a force on the ends of the lumen, thereby incrementally expanding the length of the lumen until the spring 10 has reached its expanded configuration.

Figure 3:
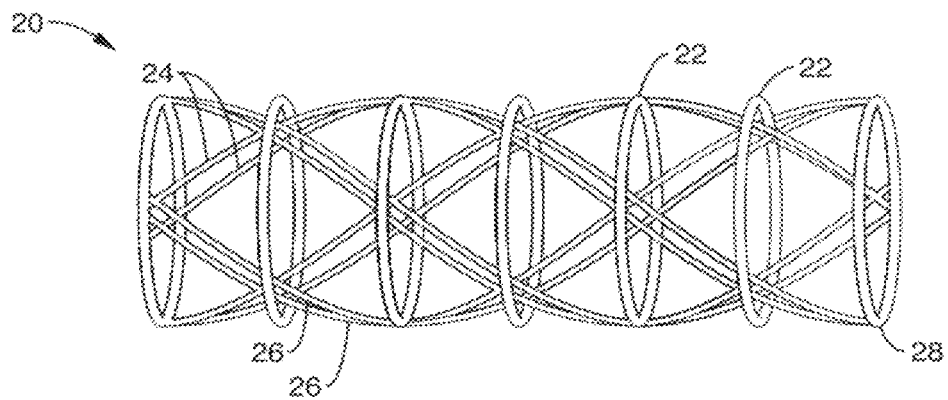
FIG. 3 is a perspective view of an alternative distension spring in accordance with the present invention.

FIG. 3 illustrates an alternative spring stent 20 having multiple undulating longitudinal wire segments 24 and 26 that wind in opposite directions with respect to each other. At the junctions of longitudinal wires 24, 26 are a series of axially spaced rings 22 at constant intervals along the length of the spring.

Figure 4:
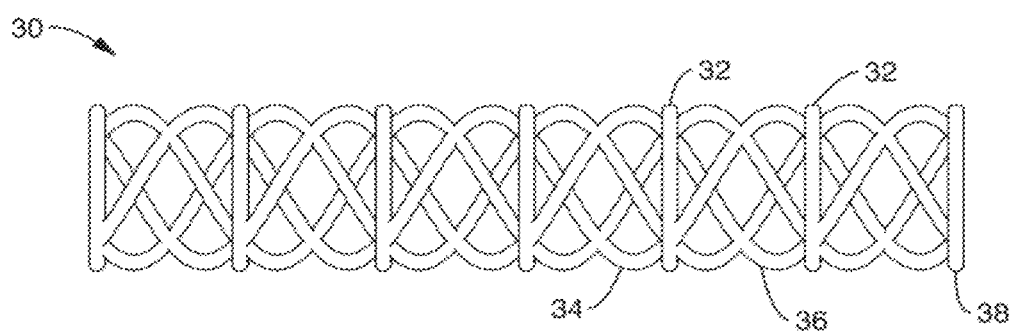
FIG. 4 is a perspective view of another alternative distension spring in accordance with the present invention.

FIG. 4 shows another spring stent 30 with undulating longitudinal wire segments 34 and 36 that have a tighter pitch P and thicker gauge to generate a larger force on the lumen. Loops 32 may correspondingly have a thicker gauge.

The end loops 28, 38 are preferably configured to engage the inner wall of the lumen upon delivery to the treatment location, such that the compressed energy of the spring is released into the walls of the lumen, and therefore affect incremental lengthening of the lumen. Thus, the end loops 28, 38 act as anchors that radially expand to engage the lumen at a dimension larger than the internal diameter of the lumen. Various means may be used to achieve said radial expansion, including oversized loops, different shapes (e.g. a triangular shape that collapses upon inward radial restraint), or other radial extension means.

With the use of the junctions shown in stents 20, 30, established large stress concentrations can lead to induced martensitic transformation in pseudo elastic wire. The spring stents 20, 30 may be configured so that they do not expand or contract significantly in the radial direction, but instead release their energy from the compressed state into axial deformation.

Figure 5:
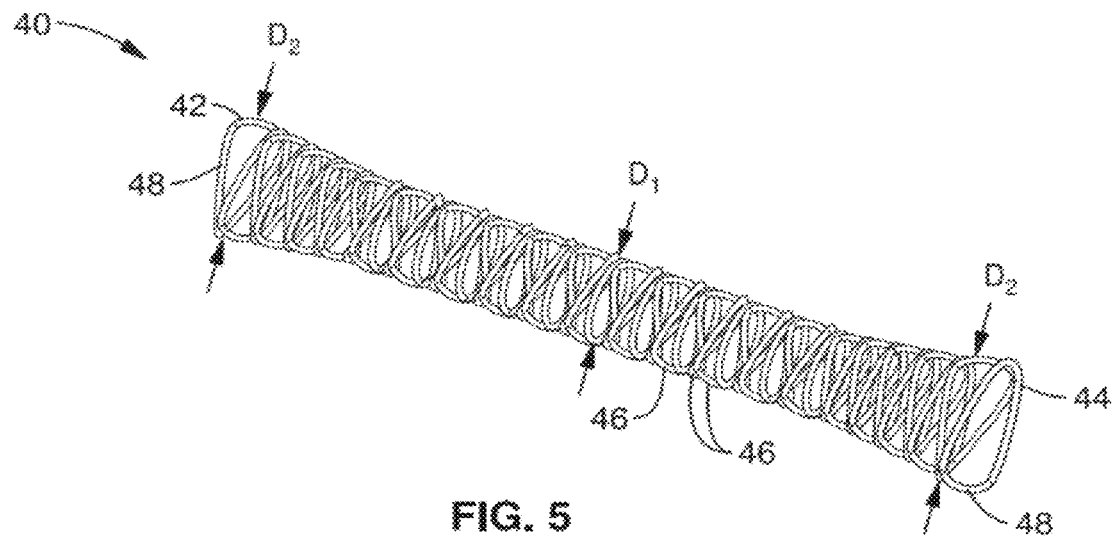
FIG. 5 is a perspective view of an alternative distension spring having lateral anchoring means in accordance with the present invention.

FIG. 5 illustrates a spring stent 40 having enlarged ends 42 and 44 for engaging and anchoring the internal wall of the lumen. The stent 40 comprises a plurality of interconnecting members 46 that intersect at a plurality of junctions. The spring stent 40 may be laser cut from one piece of material, or may be a weave of wires. The end loops 48 have a diameter $D_2$ that is larger than the diameter $D_1$ at the middle section, and the ends preferably taper from $D_1$ to $D_2$, while leaving a constant diameter along the majority of the length of the stent 40.

Figure 6:
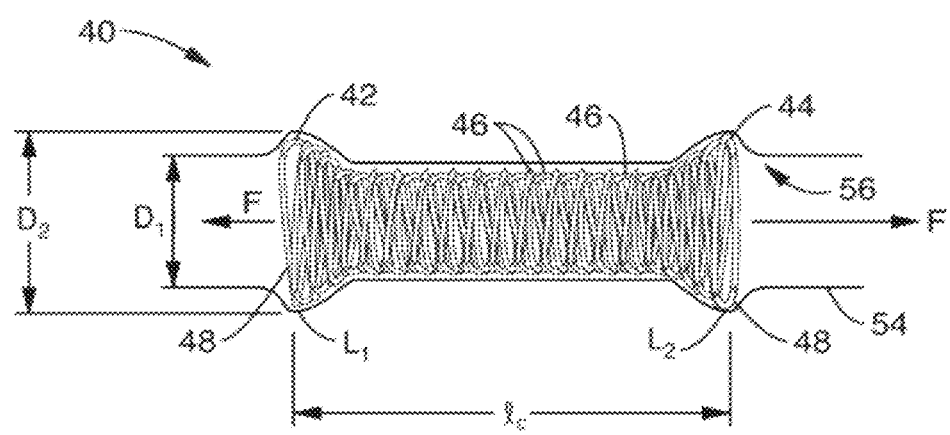
FIG. 6 illustrates the distension spring stent of FIG. 5 implanted in a radially expanded and axially compressed configuration in a body lumen.

FIG. 6 illustrates the stent 40 delivered in an axially compressed, but radially expanded state in a lumen (e.g. bowel segment) 54. The ends 48 of the stent 40 expand to a diameter $D_2$ that is larger than the diameter $D_1$ of the interior wall 56 of the lumen 54, thereby stretching the lumen and anchoring the stent at locations $L_1$ and $L_2$. In this initial state, the stent 40 has a compressed length $l_c$, at engagement points $L_1$ and $L_2$. The spring stent 40 then exerts an axial force F on the lumen 54 to incrementally lengthen the lumen 54 until the distance between points $L_1$ and $L_2$ matches the expanded stent distance $l_e$.

It is appreciated that the added rigidity (e.g. particularly in bending) of spring stents 20, 30, and 40 helps to avoid buckling of the stent during deployment and expansion. Thus, a distension system 60 using any of stents 20, 30 and 40 may not include the longitudinal support 66, as may be needed for the coil spring 10 of FIG. 1.

The stent structures 10, 20, 30, 40 are preferably may from a memory material, such as of Ni—Ti wire, also known as Nitinol, using a process called "shape setting heat treatment," during which Ni—Ti wire is wrapped around a mold and heated to 480° C. for 20 minutes followed by rapid cooling. Other memory materials possible are NiTiCu, NiTiPt and a host of other materials including the new ferromagnetic shape memory alloys such as NiMnGa.

Nickel Titanium (Ni—Ti) is a unique material that exhibits a thermally induced crystalline transformation between martensitic phase, a low temperature phase, and austenitic phase, a high temperature phase. The temperature at which martensitic and austenitic phase begin and finish forming are represented by martensite start ($M_s$), martensite finish ($M_f$), austenite start ($A_s$) and austenite finish ($A_f$) temperatures. The austenitic phase of Ni—Ti is a highly ordered body centered cubic structure, B2 phase. In the martensitic phase (i.e., low temperature), it is a monoclinic crystal structure, B19' phase. The temperature at which these phase change takes place depends on Ni and Ti ratio. A small change in Ni content leads to a large change in its transformation temperatures. For example changing from form $Ni_{52}Ti_{48}$ to $Ni_{48}Ti_{52}$ the transformation temperatures change from −100° C. to 120° C. Hence, by changing a specific Ni and Ti content the transformation temperatures can be fixed at a desired operating temperature. The composition is extremely important for applications requiring either shape memory behavior or pseudo elastic behavior.

Shape memory behavior is unique to a specific class of material. When the material is in martensitic phase, i.e. $T<M_f$, mechanical loading gives rise to an initial elastic deformation followed by pseudo yielding producing strains up to 10%. Upon unloading the strain reduces a little and the large strain produced during loading remains as residual strain (i.e.=10%). The residual strain produced can be completely recovered by heating the material above $A_f$. This recoverable deformation by the application of heat is termed the shape memory effect. In the martensitic phase (i.e. low temperature) the material has twinned structure and the observed pseudo yielding is due to twin boundary motion. Strain produced due to twin boundary motion remains even after the removal of the mechanical load. When the material is heated to above $A_f$, the material changes its crystalline phase from martensitic to austenitic phase recovering virtually all of the deformation produced by twin boundary motion.

Pseudo-elasticity is another unique behavior observed in Ni—Ti class of materials. When the material is in austenitic phase, i.e. $T>A_f$, mechanical loading induces an elastic deformation until induced martensitic phase transformation occurs at nearly constant stress. This produces relatively large deformation, up to 10%, due to twin boundary motion and recovers completely upon release of the stress. In other words, a constant force/stress is generated when the material is pre-strained. To observe the pseudo elastic behavior around body temperature, the $A_f$ temperature is fixed just below body temperature by varying Ni content. In addition, the material also shows excellent biocompatibility and fatigue resistance.

Figure 7:
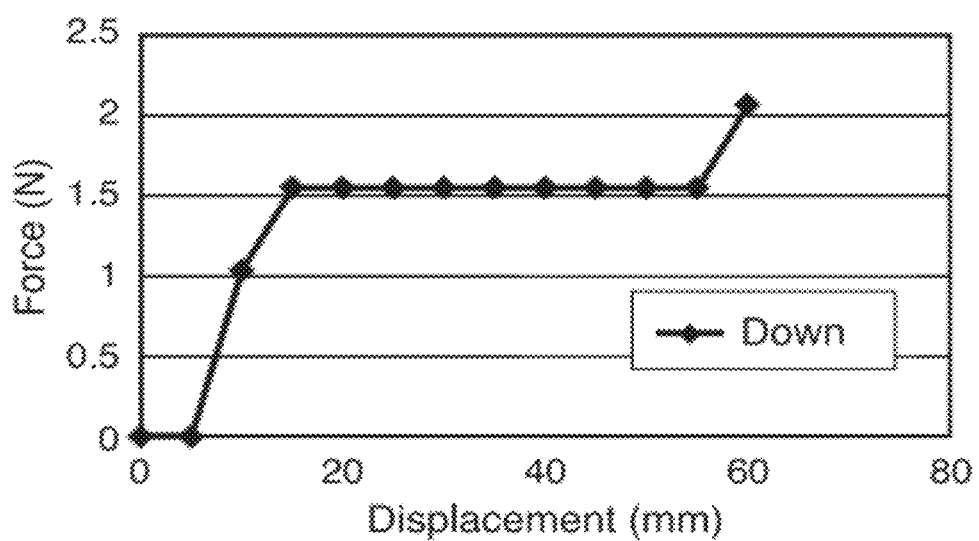
FIG. 7 is a graph showing the applied force as a function of displacement of a Nitinol distension spring in accordance with the present invention.

As seen in FIG. 7, Ni—Ti has important characteristics of pseudo elastic behavior of constant force generation and a large reversible deformation over a long activation period. The constant force can be adjusted over a wide range by varying composition and thermo-mechanical treatment.

The Nitinol spring stents of the present invention are configured to have a composition that produces a transformation temperature below body temperature and thus exhibits superelastic properties (i.e. stress induced phase transformation). That is, the superelastic properties of the wire are utilized rather than the shape memory properties normally associated with Nitinol.

EXAMPLE

FIGS. 8A-B show a test setup of the distension system 80 of the present invention using a nickel titanium spring driven tissue expansion system in a deployable configuration. FIG. 8A shows an exemplary Nitinol spring stent 10 in its uncompressed-extended form. Springs were made using the shape setting heat treatment process during which a Nitinol wire was wrapped around a mold and heated to 480° C. for 20 minutes, followed by rapid cooling. The Nitinol material had a composition that produced a transformation temperature below body temperature and thus exhibited superelastic properties (i.e. stress induced phase transformation).

Prior to implantation, the spring was placed over a piece of dissolvable number 12 spaghetti (F.Lli De Cecco Di Filippo, Martino, Italy) to allow for uniformity of the spring once compressed. Springs were 3.4 mm in diameter and delivered an average force of 1.7 Newtons (range=1.3-2.2N). A straight Nitinol wire 66 was also placed longitudinally through the spring to prevent buckling of the spring upon deployment. Next, 10 French latex catheter tips 62, 64 (Bard, Covington, Ga.) were placed over the ends of the spring to protect the intestinal segment. The spring was then compressed using 5-0 fast absorbing plain gut sutures for the experimental arm and 5-0 Ethilon sutures for the control arm. The excess spaghetti left behind after spring compression was then cut adjacent to the ends of the spring, while the straight wire was cut 1 cm away from the spring ends (FIG. 8B).

Initial experiments were conducted to establish the optimal force of springs and system configuration. Springs with varying forces were implanted to determine the optimal strength at which lengthening was achieved without perforating the intestinal segments. Several types and sizes of suture material (5-0 chromic gut, 5-0 plain gut, 6-0 fast absorbing plain gut, Ethicon, Cincinnati, Ohio) were also tested to vary the time to spring deployment with each suture. Finally, different combinations of dissolvable (e.g. spaghetti) and non-dissolvable (straight metal wire) material were used to test effectiveness in holding the spring in place and preventing buckling.

Once the optimal tissue expander device specifications were determined, specimens were divided into two groups: a control group (n=7) which underwent placement of springs compressed with 5-0 Ethilon non-absorbable suture (Ethicon, Cincinnati, Ohio) and an experimental group (n=5) which underwent placement of springs compressed with 5-0 fast absorbing plain gut absorbable suture (Ethicon, Cincinnati, Ohio). Animals were monitored with weekly x-rays following tissue expander placement.

For the procedure, a midline laparotomy was performed, from which the intestines were eviscerated. A segment 82 of jejunum 84 approximately 10 cm distal to the pylorus and corresponding to the length of the tissue expander device was isolated. Care was taken to select a segment with its own blood supply that arose as close to the base of the mesentery as possible to allow for increased mobility of the isolated segment. The distension system 80 was then inserted into the lumen of the isolated intestinal piece 82 and the ends were oversewn with 6-0 Prolene sutures (Ethicon, Cincinnati, Ohio) in an interrupted fashion, leaving the straight wire tips protruding out (FIG. 9). The continuity of the remaining intestine was restored using interrupted 6-0 Prolene sutures. Intestines were then returned back into the abdominal cavity, and the abdominal wall was closed using running sutures of 4-0 Vicryl and 4-0 Ethilon (Ethicon, Cincinnati, Ohio) for the muscle and skin layers respectively.

Beginning on post-operative day 7, animals underwent posterio-anterior and lateral abdominal x-rays each week to assess spring expansion.

Initial experiments identified 5-0 fast absorbing plain gut suture as the most optimal suture material to use, dissolving and thus deploying the spring between 3 and 7 weeks. Other sutures either dissolved too quick (6-0 fast absorbing plain gut, 1 week), too late (5-0 chromic gut, >2 months) or at variable time points (5-0 plain gut, 3 weeks to >2 months).

In addition, it was found that placing the spring 10 over a piece of absorbable material (e.g. spaghetti) facilitated insertion into the intestinal segment 82 by preventing curving of the ends. With the dissolution of the spaghetti however, there was a tendency for the spring to buckle and form a sphere intraluminally (FIG. 10A). For this reason, subsequent devices were designed to include placement of the straight metal wire 66 through the spring 10 prior to implantation and substantially maintain the longitudinal shape of the spring through expansion (FIGS. 10B, C).

Intestinal segments were successfully lengthened in the experimental group from 1.3±0.3 cm to 4.4±0.5 cm (p<0.001). Maximum spring length was achieved on postoperative day 36 (range 16-50 days). In the control group, there was also an increase in intestinal lengths, from 1.6±0.04 cm to 2.9±0.4 cm (p<0.001) (FIG. 11A). However, in terms of percentages, a 250% increase in length was observed in the experimental group (FIG. 11B) versus an 85% increase in the control group (p<0.001). Intestinal segment weights were 1.8±1.2 g in experimental group vs. 0.9±0.2 g in control group (p=0.1).

FIGS. 12 A-C are images of hematoxylin and eosin staining of intestinal segments depicting preserved intestinal architecture with muscular hypertrophy and villous atrophy in both control (FIG. 12A) and lengthened (FIG. 12B) segments in comparison to in-continuity (FIG. 12C). Microscopic evaluation of both control and experimental segments revealed gross preservation of intestinal architecture, however muscular layer hypertrophy and villous atrophy was noted.

A significant advantage of the distension system of the present invention stems arise the fact that the device does not have an external component that is outside the abdominal cavity and does not require repeated interventions during the lengthening process. Furthermore, the distension system of the present invention may be deployed endoscopically, eliminating the need for a laparotomy. Endoscopic placement of the distension system allows for successful lengthening of intestinal segments without the need to remove them from continuity with the rest of the gastrointestinal tract. These advantages are especially important in the setting of patients with SBS, nearly all of whom have a history of prior abdominal operations. While the ultimate goal is to deploy this device endoscopically, the purpose of the present study was to conclusively demonstrate its ability to lengthen intestinal segments by isolating a portion of the proximal jejunum. However, the distension system of the present invention may also achieve these results when deployed in non-isolated intestinal segments.

Another benefit of the distension system of the present invention lies in its ability to take advantage of the properties of Nitinol. For superelastic compositions, an applied stress induces a phase transformation producing up to 10% strain that is completely recoverable upon removal of the stress. A unique attribute, in addition to this relatively large recoverable strain (i.e. most metals are limited to 1% strain), is the stress in the material remains relatively constant even though the material undergoes very large elongations. Therefore, the distension device of the present invention is configured to deliver a substantially constant force on the intestinal segment throughout the very long lengthening procedure.

Given the ability of the spring to coil or assume a non-linear conformation during expansion, the potential for continued lengthening even past the linear limitations of the abdominal cavity is yet another advantage of distension system of the present invention. Unlike other devices that are rigid and can only traverse the distance between one side of the abdominal wall to the other, the flexible nature of the spring stent of the distension system of the present invention allows for much higher-fold lengthening. Additionally, given its potential for endoscopic application, this distension system of the present invention is adapted to be serially compressed and re-deployed, again allowing for higher-fold lengthening without the need for repeated trans-abdominal interventions.

While the above description is focused primarily on intestinal lengthening, it is appreciated that the distension system of the present invention may also have use in lengthening other hollow viscous organs, such as the esophagus or vagina.

The lengthened bowel segments were noted to have intestinal wall thickening, primarily due to hypertrophy of the muscular layers. This hypertrophy appears to be a physiologic response to the applied mechanical forces as well as removal of segments from intestinal continuity.

In addition, villous atrophy was noted in all experimental as well as control segments. This can in part be explained by the buildup of mucous and subsequent increase in intraluminal pressure inside the isolated segments. If it is found that villous atrophy significantly affects the absorptive functions of intestinal segments, the method of the present invention may include performing either an external or internal draining procedure to decompress the mucous.

The variability in the time to device deployment in vivo, e.g. via selection of absorbable suture materials, may also be varied, to allow for immediate intra-operative deployment. This may allow for a shorter time to maximal lengthening and may lead to less mucous buildup and subsequent villous atrophy.

From the discussion above it will be appreciated that the invention can be embodied in various ways, including the following:

1. A mechanical distension apparatus, comprising: an elongate, tubular structure configured to be inserted into a body lumen at a treatment location within the lumen; the tubular structure comprising a central axial channel configured to allow normal operation of said lumen; said tubular structure having first and second ends and being compressible along a longitudinal axis between said ends to form an axially compressed configuration; said tubular structure having at least two spaced apart anchor portions configured to engage an internal wall of the lumen at said treatment location while in said axially compressed configuration; and wherein the tubular structure is biased to elongate to an expanded configuration, said bias configured to impart a force on the lumen at said treatment location to lengthen the lumen at said location.

2. An apparatus as recited in embodiment 1: said tubular structure being formed from a shape memory material; wherein the tubular structure is biased to elongate to the expanded configuration by memory effect.

3. An apparatus as recited in embodiment 2, wherein said shape memory material comprises nickel titanium.

4. An apparatus as recited in embodiment 3, wherein the shape memory material is configured to have a composition that produces a transformation temperature below body temperature such that the tubular structure is substantially superelastic.

5. An apparatus as recited in embodiment 1, wherein the tubular structure comprises a wire-frame spring stent structure comprising a plurality of coils.

6. An apparatus as recited in embodiment 5, the plurality of coils having a pitch and gauge configured to deliver a predetermined force to the lumen at said anchor points.

7. An apparatus as recited in embodiment 1, wherein at least a portion of said tubular structure is radially compressible into a radially compressed configuration.

8. An apparatus as recited in embodiment 7, wherein said two spaced apart anchor portions are configured to compress into the radially compressed configuration during delivery into the lumen, and expand into a radially expanded configuration to engage the internal wall of the lumen.

9. An apparatus as recited in embodiment 1, wherein the tubular structure comprises a wire-frame spring stent structure comprising a plurality of undulating longitudinal wire segments coupled to a plurality of axially spaced rings.

10. An apparatus as recited in embodiment 9, wherein the undulating longitudinal wire segments comprise a first wire segment that is wound in a direction opposite to a second wire segment, and meet at one or more junctions across the length of the stent.

11. An apparatus as recited in embodiment 10, wherein the plurality of axially spaced rings are located at said one or more junctions.

12. An apparatus as recited in embodiment 1, wherein the tubular structure comprises: a spring stent structure comprising a plurality of interconnecting members that intersect at a plurality of junctions; the spring stent structure comprising a middle section comprising a first diameter configured to conform to a diameter of the internal wall of the lumen, and end portions disposed on opposite sides of said middle section; wherein said end portions have a second diameter that is larger than the internal wall diameter so as to engage an internal wall of the lumen.

13. A distension system for lengthening a segment of a luminal hollow organ, comprising: an elongate tubular structure configured to be inserted into a body lumen at a treatment location within the lumen; the tubular structure comprising a central axial channel configured to allow normal operation of said lumen; said tubular structure having first and second ends and being compressible along a longitudinal axis between said ends to form an axially compressed configuration; said tubular structure having at least two spaced apart anchor portions configured to engage an internal wall of the lumen at said treatment location while in said axially compressed configuration; wherein the tubular structure is biased to elongate to an expanded configuration, said bias configured to impart a force on the lumen at said treatment location to lengthen the lumen at said location; and an absorbable retaining element configured to retain the tubular structure in its axially compressed configuration; wherein the retaining element is configured to dissolve after a period of time within the lumen to free the tubular structure to impart said force on said lumen.

14. A system as recited in embodiment 13, further comprising: an insertion tube configured to deliver the tubular structure in the axially compressed configuration to the treatment location.

15. A system as recited in embodiment 13, wherein the tubular structure comprises a Nitinol composition that produces a transformation temperature below body temperature such that the tubular structure is substantially superelastic.

16. A system as recited in embodiment 13, wherein the tubular structure comprises a wire-frame spring stent structure comprising a plurality of coils.

17. A system as recited in embodiment 16, further comprising: a longitudinal support member configured to be positioned in the central channel of the tubular structure.

18. A system as recited in embodiment 13, wherein the tubular structure comprises a wire-frame spring stent structure comprising a plurality of undulating longitudinal wire segments coupled to a plurality of axially spaced rings.

19. A system as recited in embodiment 13, wherein the retaining element comprises an absorbable suture.

20. A system as recited in embodiment 14, wherein at least a portion of said tubular structure is radially compressible into a radially compressed configuration; and wherein the tubular structure is configured to be delivered to the treatment location in said insertion tube while in a radially and axially compressed configuration.

21. A method for distending a hollow organ comprising: providing an elongate, tubular structure configured to be inserted into a body lumen at a treatment location within the organ; the tubular structure comprising a central channel configured to allow normal operation of said organ; said tubular structure having first and second ends and being compressible along a longitudinal axis between said ends to form an axially compressed configuration; said tubular structure having at least two spaced apart anchor portions configured to engage an internal wall of the lumen at said treatment location while in said axially compressed configuration; and wherein the tubular structure is biased to elongate to an expanded configuration, said bias configured to impart a force on the organ; compressing said tubular structure along said longitudinal axis; retaining said tubular structure in an axially compressed state; inserting said compressed tubular structure into said organ and positioning said tubular structure adjacent said location wherein said at least two anchor portions engage said organ and hold said tubular structure in position; and expanding the tubular structure to an expanded configuration to lengthen the organ at said treatment location.

22. A method as recited in embodiment 21, wherein retaining said tubular structure in an axially compressed state comprises securing the tubular structure with a dissolvable suture material.

23. A method as recited in embodiment 21, wherein expanding the tubular structure comprises: allowing said suture material to dissolve freeing said tubular structure to expands along said axis.

24. A method as recited in embodiment 21, further comprising: radially compressing said tubular structure prior to insertion into said organ; retaining said tubular structure in a radially compressed state using a delivery device; and removing said delivery device after insertion and positioning of said tubular structure; wherein said tubular structure radially expands and said at least two anchor portions engage said organ.

25. A method as recited in embodiment 24, wherein said delivery device comprises a catheter.

26. A method as recited in embodiment 21, wherein said organ comprises an intestine.

27. A method as recited in embodiment 26, wherein the delivery device is configured to deploy the tubular structure endoscopically.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A mechanical distension apparatus for treating a luminal organ, comprising:
   an elongate, tubular structure configured to be inserted into a luminal segment of the intestines, esophagus or vagina at a treatment location within the luminal segment;
   the tubular structure comprising a central axial channel configured to allow normal operation of said lumenal segment;
   said tubular structure having first and second ends and being compressible along a longitudinal axis between said ends to form an axially compressed configuration;
   said tubular structure having at least two spaced apart anchor portions configured to engage an internal wall of the luminal segment at said treatment location while in said axially compressed configuration; and
   wherein the tubular structure is biased to elongate to an expanded configuration, said bias configured to impart a force on the luminal segment at said treatment location to lengthen the luminal segment at said location.

2. An apparatus as recited in claim 1:
   said tubular structure being formed from a shape memory material;
   wherein the tubular structure is biased to elongate to the expanded configuration by memory effect.

3. An apparatus as recited in claim 2, wherein said shape memory material comprises nickel titanium.

4. An apparatus as recited in claim 3, wherein the shape memory material is configured to have a composition that produces a transformation temperature below body temperature such that the tubular structure is substantially superelastic.

5. An apparatus as recited in claim 1, wherein the tubular structure comprises a wire-frame spring stent structure comprising a plurality of coils.

6. An apparatus as recited in claim 5, the plurality of coils having a pitch and gauge configured to deliver a predetermined force to the luminal segment at said anchor points.

7. An apparatus as recited in claim 6, wherein at least a portion of said tubular structure is radially compressible into a radially compressed configuration.

8. An apparatus as recited in claim 7, wherein said two spaced apart anchor portions are configured to compress into the radially compressed configuration during delivery into the luminal segment, and expand into a radially expanded configuration to engage the internal wall of the luminal segment.

9. An apparatus as recited in claim 8:
   wherein said two spaced apart anchor portions are configured to attach to a lumen of an abdominal organ; and
   wherein the predetermined force is configured to impart a force sufficient to lengthen at least a portion of the abdominal organ.

10. An apparatus as recited in claim 9, wherein the abdominal organ comprises an intestinal segment.

11. An apparatus as recited in claim 1, wherein the tubular structure comprises a wire-frame spring stent structure comprising a plurality of undulating longitudinal wire segments coupled to a plurality of axially spaced rings.

12. An apparatus as recited in claim 11, wherein the undulating longitudinal wire segments comprise a first wire segment that is wound in a direction opposite to a second wire segment, and meet at one or more junctions across the length of the stent.

13. An apparatus as recited in claim 12, wherein the plurality of axially spaced rings are located at said one or more junctions.

14. An apparatus as recited in claim 1, wherein the tubular structure comprises:
   a spring stent structure comprising a plurality of interconnecting members that intersect at a plurality of junctions;
   the spring stent structure comprising a middle section comprising a first diameter configured to conform to a diameter of the internal wall of the lumen, and end portions disposed on opposite sides of said middle section;
   wherein said end portions have a second diameter that is larger than the internal wall diameter so as to engage an internal wall of the luminal segment.

15. A distension system for lengthening a segment of a luminal hollow organ, comprising:
   an elongate tubular structure configured to be inserted into a luminal segment of the intestines, esophagus or vagina at a treatment location within the luminal segment;
   the tubular structure comprising a central axial channel configured to allow normal operation of said luminal segment;
   said tubular structure having first and second ends and being compressible along a longitudinal axis between said ends to form an axially compressed configuration;
   said tubular structure having at least two spaced apart anchor portions configured to engage an internal wall of the lumen at said treatment location while in said axially compressed configuration;
   wherein the tubular structure is biased to elongate to an expanded configuration, said bias configured to impart a force on the luminal segment at said treatment location to lengthen the luminal segment at said location; and
   an absorbable retaining element configured to retain the tubular structure in its axially compressed configuration;
   wherein the retaining element is configured to dissolve after a period of time within the luminal segment to free the tubular structure to impart said force on said luminal segment.

16. A system as recited in claim 15, further comprising:
   an insertion tube configured to deliver the tubular structure in the axially compressed configuration to the treatment location.

17. A system as recited in claim 16:
   wherein at least a portion of said tubular structure is radially compressible into a radially compressed configuration; and
   wherein the tubular structure is configured to be delivered to the treatment location in said insertion tube while in a radially and axially compressed configuration.

18. A system as recited in claim 15, wherein the tubular structure comprises a Nitinol composition that produces a transformation temperature below body temperature such that the tubular structure is substantially superelastic.

19. A system as recited in claim 15, wherein the tubular structure comprises a wire-frame spring stent structure comprising a plurality of coils.

20. A system as recited in claim 19, further comprising:
   a longitudinal support member configured to be positioned in the central channel of the tubular structure.

21. A system as recited in claim 15, wherein the tubular structure comprises a wire-frame spring stent structure comprising a plurality of undulating longitudinal wire segments coupled to a plurality of axially spaced rings.

22. A system as recited in claim 15, wherein the retaining element comprises an absorbable suture.

23. A system as recited in claim 15:
wherein said two spaced apart anchor portions are configured to attach to a lumen of an abdominal organ; and
wherein said bias is configured to impart a force sufficient to lengthen at least a portion of the abdominal organ.

24. A system as recited in claim 23, wherein the abdominal organ comprises an intestinal segment.

\* \* \* \* \*